US009975833B2

(12) United States Patent
Devon

(10) Patent No.: US 9,975,833 B2
(45) Date of Patent: May 22, 2018

(54) EFFICIENT CATALYST FOR THE FORMATION OF POLYARYL HYDROCARBONS SUITABLE AS PRECURSORS FOR POLYDENTATE ORGANOPHOSPHORUS CATALYST LIGANDS

(71) Applicant: Eastman Chemical Company, Kingsport, TN (US)

(72) Inventor: Thomas James Devon, Longview, TX (US)

(73) Assignee: Eastman Chemical Company, Kingsport, TN (US)

( * ) Notice: Subject to any disclaimer, the term of this patent is extended or adjusted under 35 U.S.C. 154(b) by 0 days. days.

(21) Appl. No.: 15/253,316

(22) Filed: Aug. 31, 2016

(65) Prior Publication Data

US 2018/0057435 A1   Mar. 1, 2018

(51) Int. Cl.
C07C 15/14   (2006.01)
C07C 41/30   (2006.01)
C07C 1/32    (2006.01)

(52) U.S. Cl.
CPC .............. *C07C 41/30* (2013.01); *C07C 1/326* (2013.01); *C07C 2531/22* (2013.01)

(58) Field of Classification Search
None
See application file for complete search history.

(56) References Cited

U.S. PATENT DOCUMENTS

| | | |
|---|---|---|
| 3,527,809 A | 9/1970 | Pruett |
| 4,193,943 A | 3/1980 | Unruh |
| 4,201,714 A | 5/1980 | Hughes |
| 4,247,486 A | 1/1981 | Brewester |
| 4,277,627 A | 7/1981 | Bryant |
| 4,694,109 A | 9/1987 | Devon et al. |
| 4,755,624 A | 7/1988 | Phillips et al. |
| 4,760,194 A | 7/1988 | Phillips et al. |
| 4,774,362 A | 9/1988 | Devon et al. |
| 4,824,977 A | 4/1989 | Devon et al. |
| 4,885,401 A | 12/1989 | Billig et al. |
| 4,912,271 A | 3/1990 | Thelen et al. |
| 4,912,276 A | 3/1990 | Puckette |
| 4,939,309 A | 7/1990 | Puckette |
| 4,960,949 A | 10/1990 | Devon et al. |
| 5,061,669 A | 10/1991 | Puckette |
| 5,102,971 A | 4/1992 | Himmler et al. |
| 5,332,846 A | 7/1994 | Devon et al. |
| 5,364,950 A | 11/1994 | Babin et al. |
| 5,602,228 A | 2/1997 | Wang et al. |
| 5,789,624 A | 8/1998 | Unruh et al. |
| 5,922,898 A | 7/1999 | Miller |
| 5,929,289 A | 7/1999 | Abatjoglou et al. |
| 6,566,572 B2 | 5/2003 | Okamoto et al. |
| 7,709,659 B2 | 5/2010 | Zhang |
| 2002/0077250 A1 | 6/2002 | Eckert et al. |

FOREIGN PATENT DOCUMENTS

WO   WO 01/44147 A1   6/2001

OTHER PUBLICATIONS

Saikia, Kokil, et al.; "Synthesis of cationic rhodium(I) and iridium(I) carbonyl complexes of tetradentate P(CH2CH2PPh2)3 ligand: An implication of steric inhibition and catalytic hydroformylation reaction"; Journal of Molecular Catalysis A: Chemical, vol. 381; 2014; pp. 188-193.
Yu, Shichao, et al.; "Highly Regioselective Isomerization-Hydroformylation of Internal Olefins to Linear Aldehyde Using Rh Complexes with Tetraphosphorus Ligands"; Organic Letters, vol. 10, No. 16; 2008; pp. 3469-3472.
Copending U.S. Appl. No. 15/253,342, filed Aug. 31, 2016; Thomas James Devon.
Notice of Allowance and Fee(s) Due dated Feb. 24, 2017 received in U.S. Appl. No. 15/523,342.
Copending U.S. Appl. No. 15/253,360, filed Aug. 31, 2016; Thomas James Devon.
Office Action notification dated Feb. 27, 2017 received in U.S. Appl. No. 15/523,360.
Acros Organics, "Grignard Reagents" brochure; retrieved on-line Aug. 30, 2016 from http://www.acros.com/myBrochure/AO_Brochure-Grignard.pdf.
Agranat, Israel, et al.; "Multiple Horner-Emmons Cyclizations as a Route to Nonbenzenoid Aromatics. Synthesis of Polycyclic Dodecalenes"; J. Org. Chem., vol. 44, No. 12; 1979; pp. 1936-1941.
Berthiol, Florian et al.; "Reaction of aryl di-, tri-, or tetrabromides with arylboronic acids or alkenes in the presence of a palladium-tetraphosphine catalyst"; Journal of Organometallic Chemistry, vol. 689; 2004; pp. 2786-2798.
Colon, Ismael and Kelsey, Donald R.; "Coupling of Aryl Chlorides by Nickel and Reducing Metals"; J. Org. Chem., vol. 51, No. 14; 1986; pp. 2627-2637.
Ikoma, Yoshibaru et al.; "Halogen Selectivity in Nickel Salt-Catalyzed Cross-Coupling of Aryl Grignard Reagents with Bromochlorobenzenes—A Novel Synthetic Method of Unsymmetrical Terphenyl"; Synthetic Communications, vol. 21, No. 3; 1991; pp. 481-487.
Kranenburg, Mirko et al.; "New Diphosphine Ligands Based on Heterocyclic Aromatics Inducing Very High Regioselectivity in Rhodium-Catalyzed Hydroformylation: Effect of the Bite Angle"; Organometallics, vol. 14; 1995; pp. 3081-3089.

(Continued)

*Primary Examiner* — Sudhakar Katakam
*Assistant Examiner* — Ana Z Muresan
(74) *Attorney, Agent, or Firm* — James Arnold, Jr.

(57) ABSTRACT

The disclosure relates to the efficient preparation of aromatic hydrocarbons useful as intermediates for di-, tri-, tetra- and poly-dentate organophosphorus ligands having value in particular as hydroformylation catalysts. The use of triarylphosphine halide catalysts have been found to be more efficient in forming these intermediates by the use of excess triarylphosphine in an amount beyond what is required to form a coordination complex.

23 Claims, No Drawings

(56) References Cited

OTHER PUBLICATIONS

Maigrot, Nicole and Mazaleyrat, Jean-Paul; "New and Improved Synthesis of Optically Pure (R)- and (S)-2,2'-Dimethyl-1,1'-binaphthyl and Related Compounds"; Synthesis Communications; Mar. 1985; pp. 317-320.

Suzuki, Akira; "Recent advances in the cross-coupling reactions of organoboron derivatives with organic electrophiles, 1995-1998"; Journal of Organometallic Chemistry, vol. 576; 1999; pp. 147-168.

Van Der Slot, Saskia, et al.; "Rhodium-Catalyzed Hydroformylation and Deuterioformylation with Pyrrolyl-Based Phosphorus Amidite Ligands: Influence of Electronic Ligand Properties"; Organometallics, vol. 21; 2002; pp. 3873-3883.

Yan, Yongjun, et al.; "Retaining Catalyst Performance at High Temperature: The Use of a Tetraphosphine Ligand in the Highly Regioselective Hydroformylation of Terminal Olefins"; Adv. Synth. Catal, vol. 349; 2007; pp. 1582-1586.

Yan, Yongjun, et al.; "A Tetraphosphorus Ligand for Highly Regioselective Isomerization-Hydroformlation of Internal Olefins"; J. Am. Chem. Soc., vol. 128; 2006; pp. 16058-16061.

EFFICIENT CATALYST FOR THE FORMATION OF POLYARYL HYDROCARBONS SUITABLE AS PRECURSORS FOR POLYDENTATE ORGANOPHOSPHORUS CATALYST LIGANDS

BACKGROUND

The use of specially designed organophosphorus compounds as co-catalysts for transition metal catalysis has become very important industrially for the manufacture of many chemical products. Many of these phosphorus compounds, normally referred to as "ligands", have two or more phosphorus atoms attached to the hydrocarbon backbone in an arrangement that constitutes the unique structure of a given ligand. These can be used for hydrogenation, polymerization and carbonylation co-catalysts. The use of bidentate ligands as co-catalysts for the low pressure rhodium hydroformylation of olefins is of particularly high commercial importance. Bidentate refers to ligands that have two coordinating phosphorus sites.

There are several different classes of bidentate phosphorus-containing ligands available. Bidentate diphosphite ligands have been disclosed in U.S. Pat. No. 4,885,401 as co-catalysts with Rh in the hydroformylation of propylene. This class of bidentate ligands use a substituted bi-naphthyl or bi-phenyl backbone with oxygen linkages to the phosphite moieties connected to the 2,2' or 6,6'-positions of the binapthyl or biphenyl backbones respectively. Other bidentate trioganophosphine ligands make use of a single aromatic ring. In triorganophosphine ligands, the phosphorus atoms are connected to three carbon bonds. In this case, two diphenylphosphino groups are attached to the single aromatic ring by methylene, or short alkyl chains such as ethyl. This class is represented in U.S. Pat. Nos. 4,824,977 and 4,960,949. Yet another class of bidentate ligand is represented by having two diphenylphosphino groups attached to each other by an all aliphatic carbon connection, as for example 1,4-bis(diphenylphosphino)butane, endo-cis-2,3-bis(diphenylphosphinomethyl)[2,2,1]tricycloheptane, and trans-1,2-bis(diphenylphosphinomethyl)-3,3-dimethylcylobutane. The latter two of these ligands were disclosed as comparative examples in U.S. Pat. No. 4,960,949.

Most particularly, bidentate ligands have been prepared from 2,2'-dimethyl-1,1'-biphenyl, where two diphenylphosphino groups are attached independently to the two methyl groups. Similar useful bidentate ligands were prepared from 2,2'-dimethyl-1,1'-binapthyl and 2,2'-dimethyl-1-phenyl-1'-napthyl. This class of ligand is particularly useful in the rhodium catalyzed hydroformylation of propylene to prepare butyraldehyde with a high selectivity to the linear isomer. These ligands are disclosed in U.S. Pat. Nos. 4,694,109, 4,755,624 and 4,760,194. The preparation of the hydrocarbon precursors of the ligand is carried out by the nickel catalyzed coupling reaction of one mole of Grignard reagent with one mole of a single-halogen containing aromatic ring. This is particularly useful when preparing symmetrical hydrocarbons such as the 2,2'-dimethyl-1,1'-biphenyl and 2,2'-dimethyl-1,1'-binaphthyl, where two halves containing equivalent aromatic rings are used. The preparation of 2,2'-dimethyl-1,1'-binaphthyl is described in the journal "*Synthesis*" p. 317 (1985). A complex, bis(triphenylphosphine)Ni(II)Cl2 is used in this reaction. The Grignard is reacted with 1-bromo-2-methylnaphthalene.

There is also a need to prepare ligand hydrocarbon precursors with a plurality of coupling units. The coupling reaction to prepare symmetrical biaryl-compounds has the advantage of not producing unwanted coupling co-products because the two halves are equivalent. Thus, there are many variations of symmetrical coupling reactions that can take advantage of "one pot" or "one stage" reactions. Several of these make use of nickel catalyzed reduction of chloro or bromo containing aromatic hydrocarbons using in-situ generation of either the Grignard intermediate, when using magnesium metal, or an unspecified organometallic when using zinc metal. The resulting materials then proceed to make the symmetrical biaryl coupling product. Some of these examples are found in U.S. Pat. Nos. 5,061,669, 4,939,309 and 4,912,271.

Two reactions have the advantage of being able to prepare unsymmetrical biaryl hydrocarbons. In U.S. Pat. No. 4,760,194, the cross coupling reaction of 1-bromomagnesium-2-methyl naphthalene with 2-bromotoluene in the presence of a triphenylphosphine nickel(II)Cl2 complex formed the unsymmetrical 2,2'-dimethyl-1-phenyl-1'-naphthyl coupling product. The reaction was carried out by the addition of the Grignard reactant to the solution of 1-bromo-2-methylnaphthalene containing the nickel catalyst.

The other reaction, generally known as the "Suzuki Reaction", is a palladium catalyzed reaction of a halogen-containing aromatic compound with an aryl-boronic acid derivative in the presence of a mild base such as potassium carbonate. This very versatile reaction is used in many pharmaceutical applications. A review on Suzuki reaction is, A. Suzuki *J. Organometallic Chemistry* 576 (1999) pp. 147-168. The disadvantages of this reaction is the relatively high cost of the palladium catalyst required and the boronic acid derivatives. These materials have to be prepared from Grignard reagents and as such would incur an extra cost. The Suzuki reaction has been successful at polyarylation of di-, tri- and tetra-bromobenzene with phenylboronic acid, and 2-methylboronic acid. This reference makes use of a costly modifying ligand, cis,cis,cis-1,2,3,4-tetrakis(diphenylphosphinomethyl)cyclopentane to complete the reaction F. Berthiol et. al. *J. Organometallic Chemistry* 689 (2004) pp. 2786-2798.

In their efforts to prepare substituted biphenyls containing a single chloride, Y. Ikoma et. al. reacted ortho-tolylmagnesium bromide with 3-chloro- and 4-chloro-bromobenzene in the presence of unmodified NiCl2 catalyst *Synthetic Communications* 21 (3) pp. 481-487 (1991). Their premise for the reaction was that bromo-groups would be more reactive for coupling than the chloro group. The stoichiometric ratio of the two reactants was 1/1 of Grignard to chlorobromobenzene. The yields to the resulting 2-methyl-3'-chloro-1,1'-biphenyl was 86% and a terphenyl side product (where two Grignard reactants were coupled to the chloro-bromobenzene) was 7%. When using 4-chlorobromobenzene, the yield to the 2-methyl-4'-chloro-1,1'-biphenyl was 87% and 3% to the terphenyl side product. Ikoma noted that when a 1,2-bis(diphenylphosphino)ethane Ni(II)Cl2 (dppeNiCl2) catalyst was used under the same conditions, the yield to the mono-chloro biphenyl when using the 3-chlorobromobenzene, dropped to 75% and a slight increase in terphenyl yield to 9% was observed. In the case with dppeNiCl2 catalyst and the 4-chlorobromobenzene reaction, the yield to monochlorobiphenyl compound was 63% and the corresponding terphenyl side product was 9%. In their hands, an example was presented with bis(triphenylphosphine)Ni(II)Cl2 catalyst using the same conditions with the 4-chlorobromobenzene reactant, in this case, the yield to the desired monochlorobiphenyl dropped further to 59% with a slight increase to terphenyl coproduct of 12%. This information indicated that the triphenylphosphine modified catalyst, as practiced in their hands, was not that efficient for coupling two aryl-groups to an aromatic ring containing two halogen groups.

The capability to rationally prepare hydrocarbons with methyl groups in a specific arrangement permits the preparation of organophosphorus ligands that coordinate in a unique manner to a given transition metal catalyst. Thus, there remains a need to prepare ligand hydrocarbon precursors that have more than two coupling units and are adapted for creation of hydroformylation catalysts that are stable and highly selective for the production of oxo aldehyde products having a high linear/branched isomer ratio.

SUMMARY OF INVENTION

According to an embodiment, the disclosure teaches a method of preparing aromatic hydrocarbons for use as precursors for catalyst ligands wherein the method includes the steps of providing a nickel based catalyst solution; providing a polyhalogenated aromatic hydrocarbon comprising at least two reactive halogen groups on its ring; combining the nickel based catalyst solution and polyhalogentated aromatic hydrocarbon to form a mixture; and adding a Grignard reactant to the mixture to form an aromatic hydrocarbon adapted as a precursor for the preparation of catalyst ligands, wherein the method is illustrated by the following general reaction:

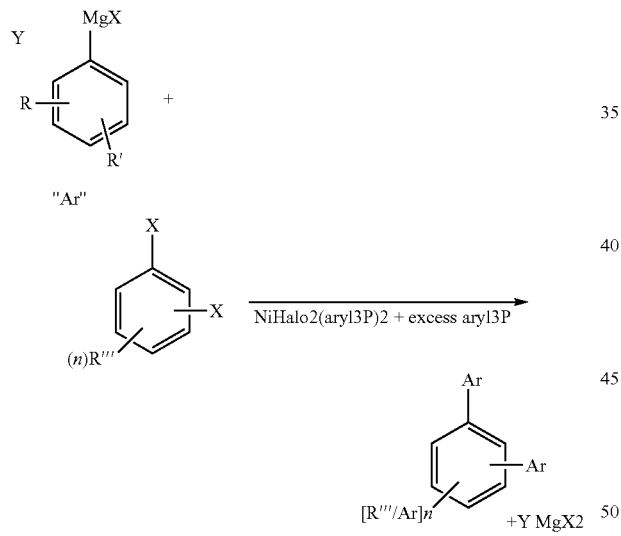

wherein,
Y=number of reactive X present on the poly halogenated aromatic
R=CH3; aryl; alkylaryl; alkyl; alkyl or aryl ether; H; thioether, or perfluoroalkyl.
R'=CH3; aryl; alkylaryl; alkyl; alkyl or aryl ether; H; thioether, or perfluoroalkyl.
X=reactive halogen groups
R'''=R, R' and/or X
n=0 to 4
Ph=Phenyl
P=Phosphorous atom
Aryl3P=Triarylphosphine
Ar=Grignard Aromatic Moiety
/=and/or Halo2=chloride or bromide
NiHalo2=Nickel Source
TPP=triphenylphosphine In alternative embodiments, the disclosure teaches the nickel based catalyst solution is prepared by the reaction of a nickel source with a triarylphosphine, including triphenylphosphine, tri(orthotolyl)phosphine, tri(p-methylphenyl) phosphine, diphenyl(o-tolyl)phosphine, diphenyl(p-methylphenyl)phosphine, or di-o-tolylyl(phenyl)phosphine. In an alternative embodiment, the nickel source is anhydrous Ni (II) chloride or bromide; or (TPP)2Ni(II)X2. In an alternative embodiment, the method of preparing aromatic hydrocarbons for use as precursors for catalyst ligands also includes adding coupling co-solvent to the mixture of the nickel based catalyst solution and polyhalogentated aromatic hydrocarbon to facilitate coupling of the mixture with the Grignard reactant, wherein the co-solvent can be diethyl ether or tetrahydrofurane.

In alternative embodiments, the disclosure teaches specific reactions corresponding to the general reaction wherein TPP=triphenylphosphine. These reactions include:

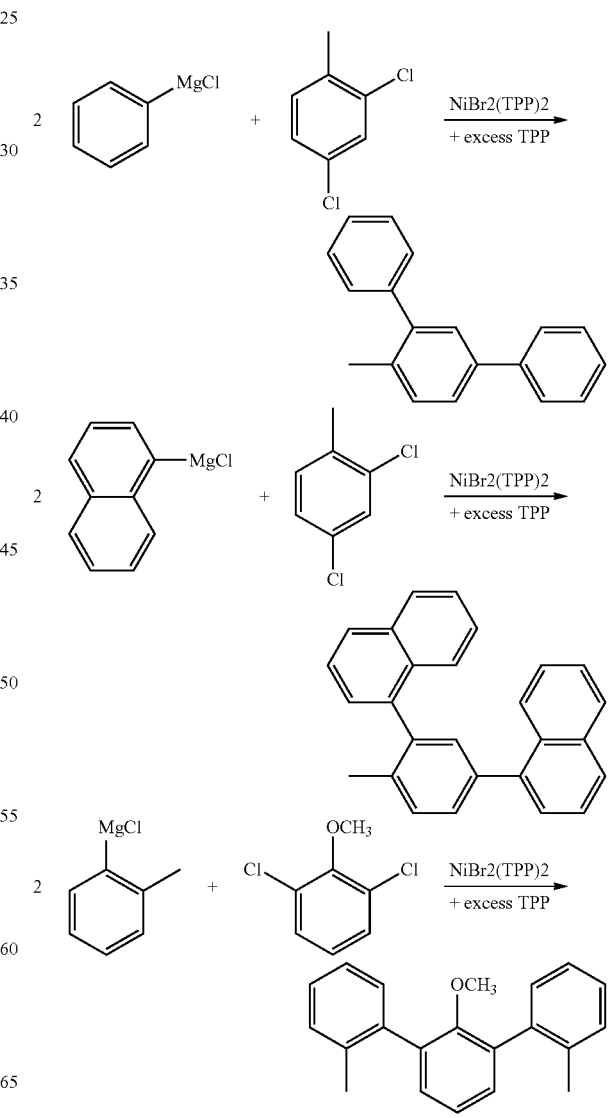

-continued

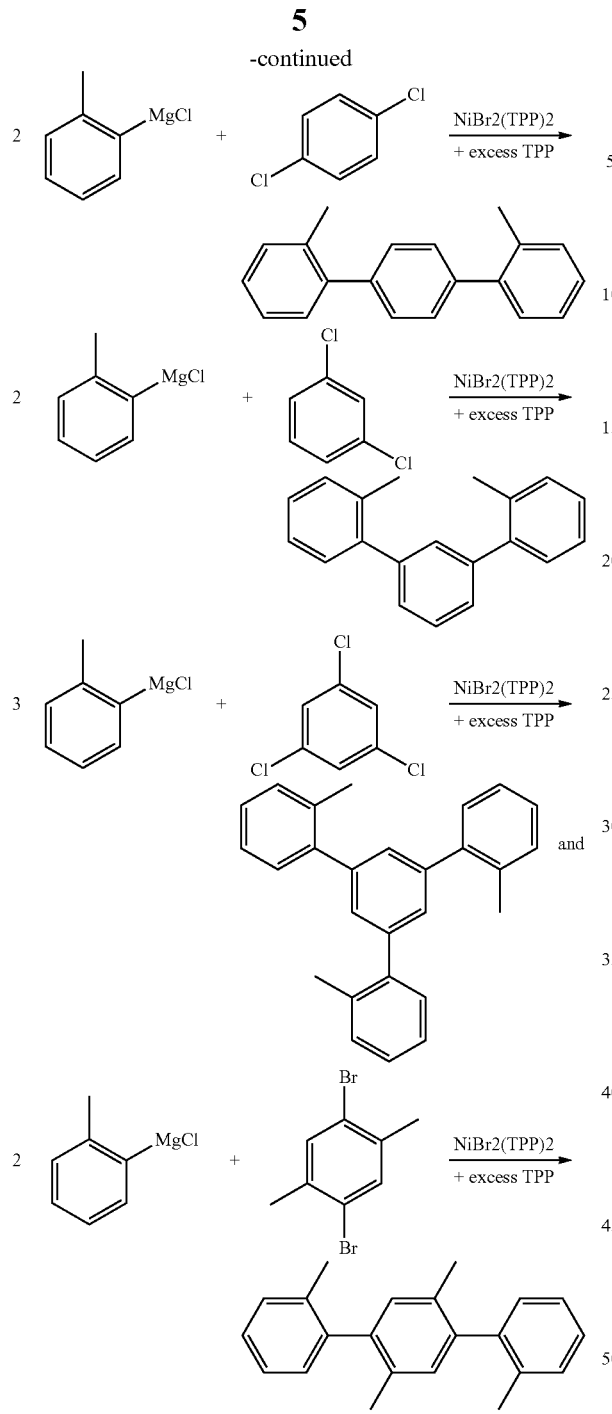

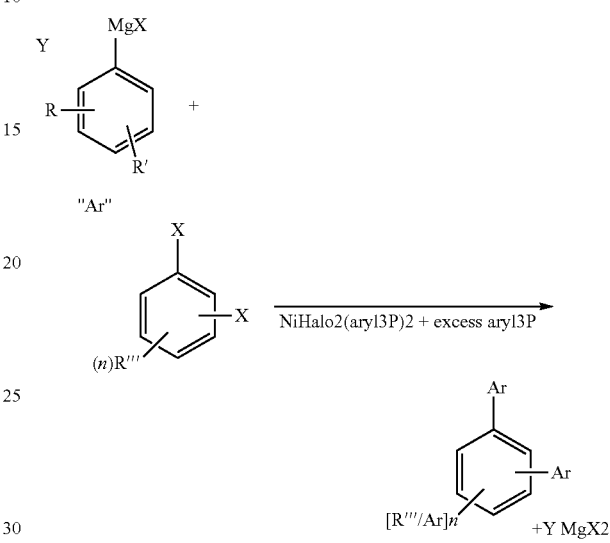

DETAILED DESCRIPTION

The disclosure relates to the efficient and rational preparation of aromatic hydrocarbons useful as intermediates for di-, tri-, tetra- and poly-dentate organophosphorus ligands having value in particular as hydroformylation catalysts. The disclosure relates to an efficient coupling catalyst capable of forming multiple carbon-carbon bonds by the reaction of aryl-Grignard reactants with aromatic hydrocarbons having two or more halogen groups present on the ring. This also can be extended to the use of aromatic hydrocarbons having more than one aromatic center with multiple halogen groups present. This could include such moieties as biphenyls, naphthalene and higher molecular weight analogues. Other organometallic reactants such as arylithium may also be contemplated. This disclosure represents an improvement in the art, whereby, the use of a bis(triphenylphosphine)Ni(II)halide catalyst is made more efficient by the use of excess triphenylphosphine above and beyond the two triphenylphosphine species required to form the complex. The general reaction is shown below:

wherein,

Y=number of reactive X present on the poly halogenated aromatic

R=CH3; aryl; alkylaryl; alkyl; alkyl or aryl ether; H; thioether, or perfluoroalkyl.

R'=CH3; aryl; alkylaryl; alkyl; alkyl or aryl ether; H; thioether, or perfluoroalkyl.

X=reactive halogen groups

R'''=R, R' and/or X

Aryl3P=Triarylphosphine n=0 to 4

P=Phosphorous atom

Ar=Grignard Aromatic Moiety

/=and/or

Halo2=chloride or bromide

NiHalo2=Nickel Source

In an alternative embodiments, n=1 to 4, n=2 to 4, or n=3 to 4. The Ni based catalyst is prepared by the reaction of anhydrous Ni (II) chloride or bromide with a triarylphosphine. In some embodiments the triarylphosphine is triphenylphosphine (TPP). In an embodiment, the mole ratio of triarylphosphine/Ni is desirably from about 2.2/1 up to about 100/1. In an alternative embodiment the mole ratio of triarylphosphine/Ni is desirably from about 10/1 up to about 100/1 or from about 5/1 up to about 10/1. Other triarylphosphines utilizing the same mole ratios of TPP/Ni may also be used in lieu of TPP. These include tri(orthotolyl)phosphine, tri(p-methylphenyl)phosphine, diphenyl(o-tolyl)phosphine, diphenyl(p-methylphenyl)phosphine, di-o-tolyl(phenyl) phosphine and the like. Optionally, the nickel source can be (TPP)2Ni(II)X2, provided that the final mole ratio of TPP/Ni is within the ranges described above. Other nickel(II) sources may be utilized The preparation is carried out by heating the nickel based catalyst and triarylphosphine in an aromatic co-solvent such as, for example toluene or xylene to reflux for a time required to form the green (TPP)2Ni(II) X2 complex solution. The aromatic co-solvent is also useful in solvating the heavy polyaromatic compound products that will be formed in the reaction. Normally thirty minutes at reflux is sufficient time to carry this out. Optionally, the poly-halogenated aromatic hydrocarbon may be included in this catalyst formation step. After forming the catalyst solution and cooling, an ether co-solvent, such as for example, diethyl ether or tetrahydrofurane (THF) is added that facilitates the coupling reaction. The amount of ether solvent added at this step is not critical, but is typically about 1/1 volume ether/volume of aromatic solvent. If the poly-halogenated aromatic has not already been added, it is added at this point.

The Grignard co-reactant is prepared by procedures well known in the art. This normally involves the reaction of a bromo- or chloro-aromatic hydrocarbon with magnesium metal in an ether solvent, such as diethyl ether, tetrahydrofurane (THF) or other ether solvents such as di-n-propyl ether, di-n-butyl ether and 1,4-dioxane. The choice of solvent is typically what is best to solubilize the resulting Grignard reactant and control the resulting boiling point of the solution. This choice is also available in the ether co-solvent used with the aromatic solvent present with the nickel catalyst.

The amount of nickel catalyst present in the coupling reaction may range from about 1/10 mole ratio of Ni/Grignard reactant to about 1/1000 mole ratio. In an alternative embodiment, the mole ratio ranges from about 1/100 to about 1/200.

The coupling reaction is carried out by the controlled addition of the Grignard reactant to the nickel catalyst solution containing the poly-halogenated aromatic reactant. The coupling reaction is carried out in an anerobic and moisture free environment. The reaction may be carried out over a wide range of temperatures from about 0 degrees Celsius up to about 100 degrees. In an alternative embodiment, from about 25 degrees to about 65 degrees. Addition times range from about one to four hours with an hour extra following the complete addition of Grignard to attain high conversion of all reactants.

This disclosure is advantaged from the standpoint of its efficiency to be highly selective to the formation of poly-arylated hydrocarbons without resorting to high ratios of excess reactant to "drive" the reaction to completion. Thus, a desirable mole ratio of Grignard reactant to poly-halogenated aromatic hydrocarbon is Y/1, where "Y" is the number of reactive halogen groups present on the poly-halogenated aromatic hydrocarbon. The catalyst of this disclosure is surprisingly so selective to the formation of poly-arylated hydrocarbons, that a mole ratio less than Y can be used to prepare poly-arylated hydrocarbons in high selectivity from the Grignard reactant while leaving much of the extra poly-halogenated aromatic hydrocarbon unconverted. Thus, the mole ratio "Y" of Grignard reactant to poly-halogenated aromatic hydrocarbon can be Y/1 or range from (Y−1)/1 to (Y+2)/1. The addition of a slight excess of Grignard reactant such as (Y+0.1)/1 may also be utilized if the total conversion of the poly-halogenated aromatic hydrocarbon is desired at the cost of extra Grignard reactant.

An object of this disclosure is to make hydrocarbon backbones suitable for being converted into polydentate organophosphorus ligands. Most of the examples given make use of Grignard reactants having methyl groups present as well as poly-halogenated aromatic hydrocarbons possessing methyl groups. The resulting methyl-containing poly-aromatic hydrocarbons are desired as they can be functionalized to the final polydentate organophosphorus ligands. This reaction can be of use in other areas, for example, precursors to specialized aromatic poly carboxylic acids for preparing specialty polyester materials, poly aromatic compounds useful for liquid crystal applications and specialty aromatic polymer intermediates.

The isolation of the poly-arylated hydrocarbons from the catalyst can be carried out by any number of means well known in the art of product isolation. The method used is normally dictated by the physical properties of the poly-arylated hydrocarbon being prepared. Thus, a distillable product may isolated by vacuum distillation from the high boiling catalyst residues. Another method often used is the oxidation of the TPP and Ni(TTP) catalyst with a small amount of hydrogen peroxide or air and the removal of the nickel by extraction with dilute acid and the removal of TPP oxide by filtration through an adsorbent such as alumina. This is often used when the poly-arylated hydrocarbon can be crystallized from solution.

While not intending to constrain the scope of this disclosure, the following specific reaction examples are presented below that correspond to the general reaction above.

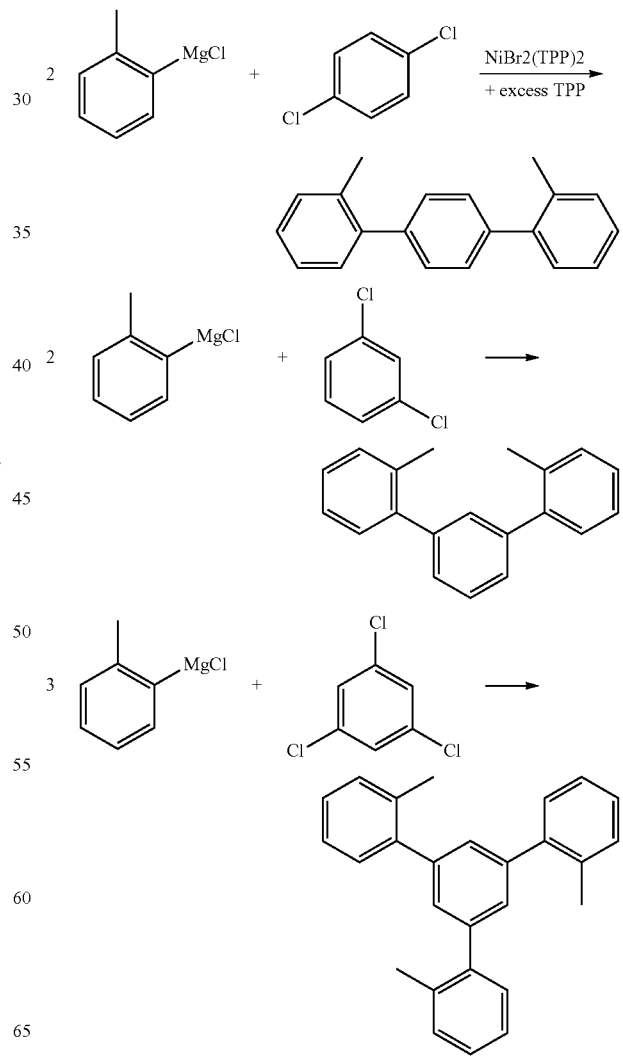

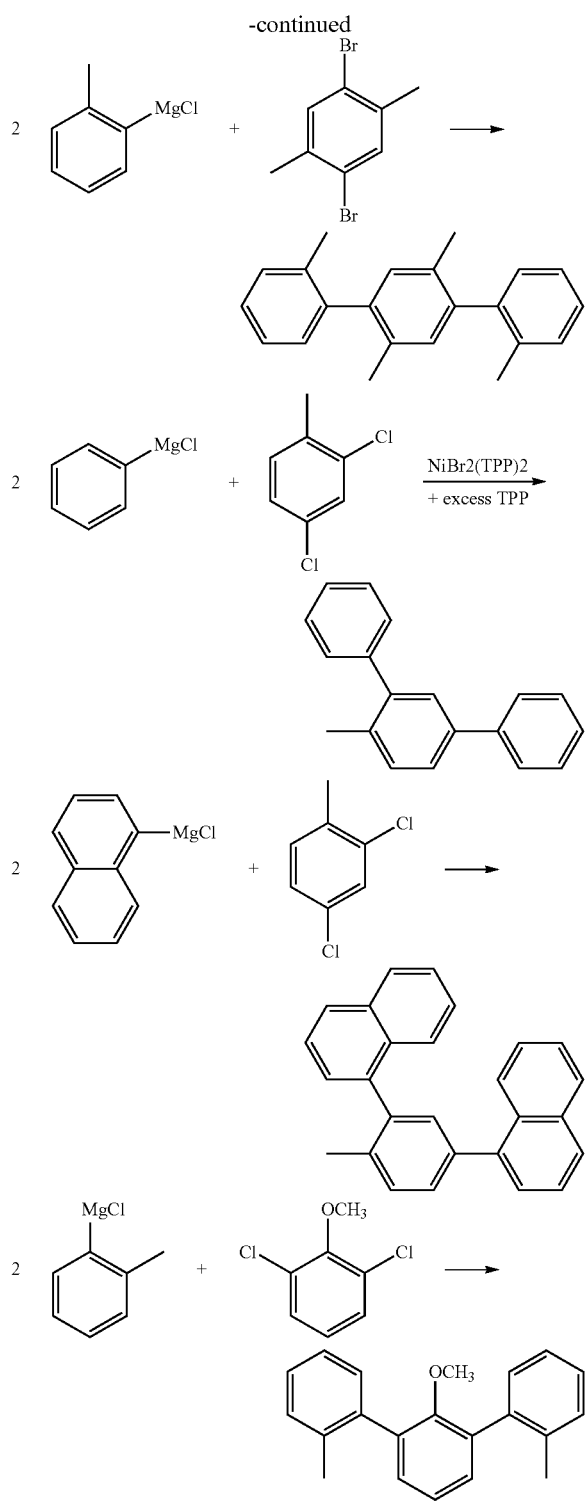

EXAMPLES

This disclosure can be further illustrated by the following examples of embodiments thereof, although it will be understood that these examples are included merely for purposes of illustration and are not intended to limit the scope of the disclosure unless otherwise specifically indicated.

Gas Chromatograph Conditions:

A Hewlett-Packard 5890 auto injector FID gas chromatograph was equipped with a J&W 30 m×0.32 mm diameter DB-5 medium film capillary column. The carrier gas was helium with a split ratio of 30/1 with an injection size of 0.2 microliters. The heat up profile was 4 minutes at 40 degrees Celsius; 10 Celsius degrees heat up/minute to 300 degrees Celsius; 32 minute hold at 300 degrees Celsius. This set of conditions was used for all samples. The aromatic solvents used in the coupling reaction were normally used as internal gas chromatographic standards. Response factors for reactants and products were determined using the aromatic solvent. Reagent grade o-xylene was used as solvent when 2-chloro or 2-bromo-magnesium toluene Grignard was used in order to account for toluene coproduct from unreacted Grignard.

Proton NMR:

The proton nuclear magnetic resonance spectra of samples were determined using an Oxford 400 Megahertz instrument. The solvents used were deuterochloroform or D6 benzene.

GC-MS:

The gas chromatographic mass spectroscopy analysis of mixtures and solutions of pure products was carried out on an Agilent 7890 Gas Chromatograph with an attached 5975B Inert XUBCI MSD mass spectrometer instrument. The column and heat up profile was chosen to match the conditions used above as closely as possible.

Examples 1 and 2 were carried out with a 1/1 mole ratio addition of Grignard reactant to 2,4-dichlorotoluene using the catalyst of this disclosure. The original intent of these runs were to prepare a mono-arylated, mono-chlorotoluene product with the arylation taking place at the 4 position of toluene. The data clearly shows the surprisingly efficient conversion of the dichlorotoluene into diarylated toluene product while leaving a large amount of 2,4-dichlorotoluene unreacted. Samples were taken during the course of the addition and also clearly showed the remarkable formation of the diarylated toluene product at low conversions of the 2,4-dichlorotoluene. The products were identified by GC-MS and the amounts were calculated using the aromatic solvent as an internal standard.

Example 1—Reaction of 1/1 Mole Ratio Phenylmagnesium Chloride with 2,4-Dichlorotoluene in the Presence of 10/1 Mole Ratio TPP/NiBr2

The apparatus was a 1-liter 3-necked flask. This was equipped with a thermocouple, a Teflon-coated efficient magnetic stirrer, a chilled glycol reflux condenser, a nitrogen atmosphere, a 250 ml pressure-equalizing addition funnel that was positioned over the center neck for direct addition to the stirred vortex of the solution and a heating mantle and magnetic stirrer.

The flask was charged with anhydrous NiBr2 (0.55 grams/ 2.5 mmole), triphenylphosphine (6.55 grams/25 mmole), and reagent grade toluene (50 milliliters/43.25 grams) as the organic solvent. The addition funnel had 2,4-dichlorotoluene (40.27 grams/0.25 mole) dissolved in 200 ml of dry THF solvent. The nickel catalyst was formed by heating the flask to reflux for 30 minutes and cooling to 50 degrees Celsius. A dark emerald green solution resulted. At this point the dichlorotoluene solution in the addition funnel was added over 3 minutes. There was no change in color. A 3 milliliter aliquot (#1) was taken for an initial GC sample. The samples were treated in the absence of air with an equal volume of 2% aqueous HCl to remove insoluble magnesium salts if present.

The addition funnel was replaced by a second 250 ml pressure-equalizing addition funnel containing 125 milliliters of 2.0 molar phenylmagnesium chloride solution (0.25 mole) in THF solvent. The temperature of the reaction flask was kept at 50 degrees Celsius for the addition. The Grignard solution was added dropwise over 2.5 hours. The green solution quickly turned to a dark red-brown after initiation of the addition. The reaction generated enough heat to require removing the heating mantle and replacing it with a hot water bath to balance the heat of reaction with cooling. Additional GC samples were taken at 50% addition (#2); 75% addition (#3); immediately following total addition of Grignard (#4); and after stirring an additional hour at 50 degrees Celsius (#5). A last sample was taken following the workup of the mixture described below (#6). The color of the mixture at the end of the addition was unchanged from the dark red-brown color formed when the addition began.

The table below records the calculated amounts of individual materials present in the mixture at the time the samples were taken. The peaks were identified by GC-MS analysis. The diarylated product, 2,4-diphenyltoluene, co-eluted with triphenylphosphine and could not be calculated until the final workup when the TPP was oxidized to the corresponding TPP oxide.

| Weights of Compounds Present in Reaction Mixture as Sampled in Grams | | | | | | |
|---|---|---|---|---|---|---|
| Sample | Benzene | 2,4-DCT | Biphenyl | 2-Ph-4-CT | 4-Ph-2-CT | 2,4-DPhT |
| 1 | 0.0 | 40.27 | 0.00 | 0.00 | 0.00 | N/A |
| 2 | 0.78 | 30.21 | 0.84 | 0.44 | 2.44 | N/A |
| 3 | 0.33 | 23.56 | 0.80 | 0.56 | 3.05 | N/A |
| 4 | 1.01 | 19.00 | 1.01 | 0.63 | 3.13 | N/A |
| 5 | 0.43 | 18.61 | 0.98 | 0.63 | 3.13 | N/A |
| 6 | 0.40 | 17.84 | 0.93 | 0.61 | 2.96 | 28.22 |

Benzene is from unreacted Grignard reactant present at the time of sampling. The 2-Ph-4-CT is the mono-arylated product at the sterically hindered 2 position and 4-Ph-2-CT is the mono-arylated product at the less hindered 4 position. 2,4-diphenyltoluene is the di-arylated product.

The work up proceeded by the addition of 200 milliliters of 10% aqueous ammonium chloride solution to the crude mixture followed by the addition of 3 ml of 50% aqueous hydrogen peroxide in 10 ml of deionized water. The resulting mixture was a two-phase liquid mixture with the organic upper layer being yellow and the lower aqueous being pale green. The organic layer was used for sample #6 and for GC-MS identification.

Based on the final sample, the conversion of 2,4-dichlorotoluene into the final products was 56%. Remarkably, the conversion of the dichlorotoluene indicated that this catalyst system primarily converted the 2,4-dichlorotoluene in high selectivity to the di-arylated product with minimal amounts of mono-arylated intermediate materials being formed throughout the course of the Grignard addition.

The final selectivities to given products based on Grignard reactant added are:
Benzene=1.9%
1,1'-Biphenyl=4.5%
2-Phenyl-4-chlorotoluene=1.1%
4-Phenyl-2-chlorotoluene=5.5%
2,4-Diphenyltoluene=87.0%

In other words, the selectivity numbers based on Grignard reactant for this Example and the others is based on the amount of Grignard fed. As an illustrative example, if 100 moles of Grignard reactant were added and the selectivity to Benzene is 1.9%, then that means that 1.9 moles of the original Grignard ended up as benzene. Under the same illustration, if the selectivity to 2,4-diphenyltoluene is 87.0% then that means that 87 moles of Grignard ended up as 2,4-diphenyltoluene.

Example 2—Reaction of 1/1 Mole Ratio of 1-Bromomagnesiumnaphthalene with 2,4-Dichlorotoluene in the Presence of 10/1 Mole Ratio TPP/NiBr2

In this example, an attempt was made to use a sterically hindered Grignard reactant to force the formation of the mono-arylated product. The data shown below indicates that the catalyst of this disclosure still favors the formation of di-arylated addition products.

The apparatus was a 1-liter three-necked flask equipped with an efficient Teflon-coated magnetic stirrer, a reflux condenser, nitrogen atmosphere, heating mantle, thermocouple, magnetic stirrer and a 250 ml pressure equalizing addition funnel. The flask was charged with clean magnesium shavings (6.56 grams/0.27 mole) an iodine crystal and 100 ml of dry THF solvent. 1-Bromonaphthalene (51.8 grams/0.25 mole) and 65 ml of dry THF solvent were in the addition funnel.

The Grignard reaction was initiated by bringing the temperature of the flask to 35 degrees Celsius and adding the bromonaphthalene solution to the flask dropwize over 2.5 hours while keeping the temperature at 35 degrees Celsius. The Grignard product began to precipitate after about 20% of the bromonapthalene addition. The addition of 20 ml of toluene and an extra 100 ml of dry THF failed to dissolve the Grignard product. The bromo addition was continued to the end, leaving a stirrable white slurry. The mixture was stirred an extra hour to complete formation of the Grignard. The material was transferred to a 500 ml pressure equalizing addition funnel. Based on a material balance at the end of the experiment, an estimated 15% of the solid Grignard was left behind. The pressure equalizing addition funnel had a large bore stopcock to help handle the slurry and a magnetic stirrer inside to be manipulated by a magnet from the outside to assist mixing during the addition of the slurry during the coupling step.

A second 1-liter three-necked flask was set up for the coupling step. The flask was equipped with an efficient Teflon-coated magnetic stirrer, a reflux condenser placed on the outside neck with an off-set adapter, a nitrogen atmosphere, thermocouple, heating mantle, magnetic stirrer and the 500 ml addition funnel containing the Grignard slurry place over the center of the flask.

The flask was charged with anhydrous NiBr2 (0.55 grams/2.5 mmole), triphenyl phosphine (6.55 grams/25 mmole), (50 milliliters/44.3 grams) of reagent grade o-xylene and 2,4-dichlorotoluene (40.27 grams/0.25 mole). This mixture was heated to reflux and held there for 30 minutes to form a dark emerald-green solution of the nickel complex. After cooling to 50 degrees Celsius, 100 ml of dry THF was added to the flask. At this point, a 3 ml aliquot of solution was taken for the initial GC sample #1.

The flask was kept between 45 and 50 degrees Celsius for the coupling step. The Grignard slurry was added in small "shots" by mixing to fluidize it and then rotating the stopcock. The addition of the Grignard immediately turned the catalyst solution to a red-orange color. At no time, were solids observed in the reaction flask. The Grignard slurry appears to have reacted upon entering the flask. The addition time was two hours. All slurry was added. The mixture was stirred at 50 degrees Celsius for an additional 2 hours. Samples from the reaction flask were taken at 50% addition (#2); 75% addition (#3); immediately following completion of the addition (#4); after being heated at 50 degrees Celsius for an extra 2 hours (#5); after standing at ambient temperature for another four days (#6) and after the crude mixture was worked up (#7).

The crude product was treated with a mixture of 135 ml of deionized water with 35 ml of concentrated hydrochloric acid and 3 ml of 50% aqueous hydrogen peroxide. The resulting two liquid phase mixture had a brown upper organic layer and a yellow aqueous layer. After separating the layers, the organic phase was washed with two 100 ml portions of 2% aqueous NaCl. The resulting organic layer was sampled for GC-MS analysis and for sample #7.

The GC-MS analysis indicated that one mono-arylated product, namely 2-chloro-4-(1'-naphthyl)toluene was found. This peak co-eluted with triphenylphosphine in our GC analysis and thus could not be quantified until the final oxidation work-up step in sample #7. Naphthalene, 1,1,'-binaphthyl, and the diarylated product 2,4-di-(1'-naphthyl)toluene were also identified. The table below lists the amounts of each compound present as grams in the reaction flask when sampled.

| Weights of Compounds Present in Mixture as Sampled in Grams | | | | | |
|---|---|---|---|---|---|
| Sample | 2,4-DCT | Naphthalene | 2-C-4-NTol | 1,1'-BiNap | 2,4-DNTol |
| 1 | 40.27 | 0.00 | N/A | 0.00 | 0.00 |
| 2 | 36.52 | 15.69 | N/A | 3.51 | 3.81 |
| 3 | 26.35 | 5.19 | N/A | 7.26 | 15.51 |
| 4 | 21.21 | 1.13 | N/A | 9.17 | 19.65 |
| 5 | 19.68 | 1.13 | N/A | 9.21 | 19.36 |
| 6 | 19.35 | 1.13 | N/A | 9.24 | 19.23 |
| 7 | 19.29 | 1.17 | 2.81 | 10.28 | 19.20 |

The conversion of 2,4-dichlorotoluene was 52%. Based on the accountable amount of Grignard added, the following selectivities to the products below are based on Grignard added.
Napthalene=4.3%
2-Chloro-4-(1'-naphthyl)toluene=5.3%
1,1'-Binapthyl=38%
2,4-Di(1'-naphthyl)toluene=52.4%

Example 3—Reaction of 2-Bromomagnesium-1,4-dimethylbenzene with 2-Bromo-1,4-dimethylbenzene in the Presence of 10/1 TPP/NiBr2

This example illustrates that the catalyst of this disclosure is also an effective coupling catalyst for preparing symmetrical sterically hindered biaryl compounds by mono-arylation reactions.

The Grignard prep was carried out in a 1-liter three-necked flask equipped with a chilled glycol reflux condenser, nitrogen atmosphere, an efficient Teflon-coated magnetic stirrer, thermowell, magnetic stirrer, heating mantle and a 250 ml pressure equalizing addition funnel. Magnesium metal shavings (7 grams/0.288 mole), a crystal of iodine, and 150 ml of dry THF solvent were added to the flask. The addition funnel was charged with 2-bromo-1,4-dimethylbenzene (46.3 grams/0.25 mole) and dissolved in 100 ml of dry THF. The Grignard reaction was initiated by bringing the reaction flask temperature to 50 degrees Celsius and adding 5 ml of the bromo-xylene solution. After the initiation, the reaction temperature was kept at 50-55 degrees Celsius for the duration of the Grignard formation. The bromo-xylene was added dropwise over approximately 2 hours. The mixture was kept at 50 degrees Celsius for an additional hour to complete the reaction. The final solution was a light brown color. After cooling, the Grignard solution was transferred by cannula under nitrogen into a 500 ml pressure equalizing addition funnel. Approximately 15% of the Grignard solution was lost to a leak in the stopcock.

The coupling reaction flask was a 1 liter three-necked flask equipped in the same manner as the Grignard flask. The 500 ml pressure equalizing addition funnel was also attached to one of the necks. Nickel bromide (0.55 grams/2.5 mmole), triphenylphosphine (6.55 grams/25 mmole), 2-bomo-1,4-dimethylbenzene (46.3 grams/0.25 mole) and reagent grade o-xylene (50 ml/44.3 grams) solvent were added. The catalyst was formed by heating the mixture to reflux and holding the temperature there for 30 minutes. After cooling to 50 degrees Celsius, 150 ml of dry THF solvent was added. The temperature in the flask was kept at 50-52 degrees Celsius for the rest of the coupling reaction. The Grignard solution was added dropwize over 3.5 hours. The green color turned to the characteristic red-brown color as the Grignard reagent was added. The mixture was stirred an additional two hours at 50 degrees to complete the reaction.

After cooling to ambient temperature, the crude mixture was treated with a mixture of 115 ml of deionized water and 35 ml of concentrated hydrochloric acid and 3 ml of 50% aqueous hydrogen peroxide. The two phase mixture was separated in a separatory funnel. The organic layer was washed with two 100 ml portions of 2% aqueous NaCl. This material was analyzed by gas chromatography. The analysis indicated a conversion of 86% of the bromoxylene. The THF and most of the xylene solvent was removed by stripping with nitrogen at ambient temperature over night to form waxy low-melting point solid. The solid was dissolved in 120 ml of mixed hexane isomers and passed through a 1"×3" diameter bed of Brockmann I alumina. The bed was washed with 2 150 ml portions of a 2/1 v/v mixture of isomeric hexane/toluene. Nitrogen stripping was used as above to remove the large majority of hexane and toluene leaving 46.6 grams of a hard waxy solid. This material was distilled in a 2 cm diameter×20 cm vacuum jacketed Vigreux column under vacuum. The desired product distilled overhead at a top take off temperature of 142-145 degrees Celsius at 9.6 mm mercury pressure (1.28 kPa). The net weight of the hard waxy solid was 31.2 grams or 59% of theoretical yield. The purity of the fraction was 99.2%. The identity of the product was confirmed by GC-MS as being 2,2',5,5'-tetramethyl-1,1'-biphenyl. The proton NMR spectrum in chemical shift relative to tetramethylsilane: 2H (D) 7.12 ppm aromatic C—H; 2H (D) 7.05 ppm aromatic C—H; 2H (S) 6.92 ppm aromatic C—H; 6H (S) 2.32 ppm 5,5' benzylic CH3; 6H (S) 2.01 ppm 2,2' benzylic CH3.

Example 4—Preparation of 2,2"-Dimethyl-1,1':3',1"-terphenyl by Reaction of 2/1 Mole Ratio of 2-Bromomagnesiumtoluene with 1,3-Dichlorobenzene in Presence of 10/1 Mole Ratio TPP/NiBr2 Catalyst This is an example of the use of this disclosure for the preparation of a specially designed terphenyl structure having two methyl groups present.

The apparatus used for the preparation of 2-bromomagnesiumtoluene is described above in example 3. The 1 liter flask was charged with magnesium metal shavings 13.7 grams/0.55 mole, an iodine crystal and 150 ml of dry THF solvent. The 250 ml pressure equalizing addition funnel was charged with 2-bromotoluene 85.5 grams/0.50 mole and enough dry THF solvent to bring the final volume to 250 ml after mixing. The temperature in the flask was brought to 35 degrees Celsius. After initiation of the Grignard reaction by the addition of 5 ml of the bromotoluene mixture, the rest of this reactant was added dropwize over 2.5 hours. The exothermic reaction in the flask was kept at 35 degrees Celsius by the use of a controlled temperature hot water bath. After cooling to ambient temperature, the resulting Grignard solution was transferred under nitrogen by cannula into a 500 ml pressure equalizing addition funnel.

The 1 liter flask and associated equipment for the coupling reaction are also described above in example 3. The flask was charged with anhydrous NiBr2 0.55 grams/2.5 mmole, TPP 6.55 grams/25 mmole, 1,3-dichlorobenzene 36.75 grams 0.25 mole and reagent grade o-xylene 50 ml/44.3 grams. The green nickel TPP complex solution was formed by heating the mixture to reflux and holding at that temperature for 30 minutes. After cooling to 50 degrees Celsius, 150 ml of dry THF solvent was added. The 500 ml pressure equalizing addition funnel containing the Grignard reactant was connected to the center neck of the coupling reaction flask.

The mixture in the flask was warmed to 50 degrees Celsius and the reaction was started by the dropwize addition of the Grignard solution to the flask. The green color changed to the characteristic red-brown color by the addition of 5 ml of the solution. The rest of the Grignard was added over 4.5 hours at 50 degrees Celsius. The mixture was stirred an extra hour at 50 degrees Celsius to complete the reaction.

After cooling to ambient temperature, the crude mixture was treated with 35 ml of concentrated hydrochloric acid dissolved in 115 ml of deionized water. To this was added 3 ml of 50% aqueous hydrogen peroxide and the mixture stirred. The two liquid phases were separated in a large separatory funnel. The upper organic layer was extracted twice with 100 ml of 1% aqueous NaCl solution. A sample of the orange organic layer was taken for gas chromatographic analysis and GC-MS analysis to identify the components present.

The gas chromatographic analysis of this crude product mixture gave the following results:
Conversion of 1,3-dichlorobenzene=99%
Selectivity of Grignard reactant to the following products:
Toluene=0.8%
2,2'-dimethyl-1,1'-biphenyl (2,2'-bitolyl)=4.2%
2-methyl-3'-chloro-1,1'-biphenyl=2.3% (this being mono-arylated product)
2,2"-dimethyl-1,1':3',1"-terphenyl=92.7% (the desired diarylation product)

The crude mixture was distilled in a vacuum distillation apparatus to remove the lower boiling solvent and coproducts. The base residue containing the product was treated with a 1/1 v/v mixture of toluene/isomeric hexane and passed through a 2.5 cm by 7.5 cm diameter bed of Brockmann I alumina and the bed was washed with two 100 ml portions of a 1/1 v/v mixture of toluene/isomeric hexane. The pale orange filtrate was stripped with nitrogen followed by subjecting the residue to 0.5 kPa pressure while being heated to 60 degrees Celsius. The net weight of very heavy light orange oil was 58.16 grams of 93% purity with a theoretical yield to desired dimethyl terphenyl product of 84%.

The proton NMR spectrum of this material in ppm relative to TMS: 12H (overlapping doublets and multiplets) 7.4-7.75 ppm aromatic C—H; 6H (S) 2.65 ppm 2,2"-benzylic CH3.

Example 5—Preparation of 2,2"-Dimethyl-1,1':4',1"-terphenyl

This is another example of the use of the disclosure for the preparation of a terphenyl having two methyl groups present.

The coupling flask was the same as described in Example 3. Anhydrous NiBr2 0.55 grams/2.5 mmole, TPP 6.55 grams/25 mmole, 1,4-dichlorobenzene 36.75 grams/0.25 mole and reagent grade o-xylene 50 ml/44.3 grams as solvent were added to the flask. The solution of green NiBr2/TPP complex was formed by heating the mixture to reflux and holding at that temperature for thirty minutes. After cooling to 50 degrees Celsius, 100 ml of dry THF solvent was added.

A 500 ml pressure equalizing addition funnel was charged with 500 ml of 1.0 molar 2-chloromagnesiumtoluene solution in THF (Aldrich) 0.50 moles and placed on the center neck of the flask. The coupling reaction was carried out at 50 degrees Celsius reaction temperature. A controlled temperature hot water bath was used to balance the heat of reaction. The Grignard solution was added dropwize over 4 hours. The mixture was stirred an additional hour to complete the reaction.

After cooling overnight to ambient temperature, the crude mixture was treated with 35 ml of concentrated hydrochloric acid with 115 ml of deionized water and then with 3 ml of 50% aqueous hydrogen peroxide. The brown organic solution had turned to an orange organic layer with a pale yellow aqueous layer. The mixture was transferred to a seperatory funnel and the aqueous layer was drained and discarded. A sample of the organic layer was taken for gas chromatographic analysis and GC-MS identification of the components. The product began to crystallize from solution when two 100 ml washes of 1% aqueous NaCl were attempted upon the organic layer. The crystals were dissolved by the addition of 100 ml of toluene and 100 ml of dichloromethane. The seperatory funnel was also warmed with a heat gun to further suppress crystallization of the product from solution. The washes proceeded normally following this.

Based on the chromatographic analysis and GC-MS identifications, the following yield information is presented below of the crude product.
Conversion of 1,4-dichlorobenzene=97%
Selectivity of Grignard reactant to a given product:
Toluene=14.4%
2,2'-Dimethyl-1,1'-biphenyl=15.1%
2-Methyl-4'-chloro-1,1'-biphenyl=1.2%
2,2"-Dimethyl-1,1':4',1"-terphenyl=69.3%

The warm organic solution from the separatory funnel crystallized on cooling to ambient temperature. The solution had been drained into a 1 liter Erlenmeyer flask. This was first warmed to dissolve the product and then slowly chilled externally by heat loss and finally with a water-ice bath to obtain white bladed crystals of product. These were collected on a glass frit and washed with isopropanol and dried under vacuum. The net weight of this first crop was 28.52 grams or 44% of theoretical yield. The mother liquors were stripped with nitrogen and vacuum to leave 29 grams of an impure crystalline solid.

The proton NMR spectrum of the pure crystalline product expressed in ppm relative to TMS:

4H (S) 7.35 ppm 2',3',5',6' aromatic C—H; 8H (overlapping multiplets) 7.25 ppm aromatic C—H on remaining aromatic rings; 6H (S) 2.30 ppm benzylic CH3.

Example 6—Preparation of 2,2"-Dimethyl-2'-methoxy-1,1':3',1"-terphenyl

This example demonstrates that the catalyst of this disclosure may be used to prepare products by the diarylation reaction that can incorporate heteroatom substituent groups, as in this case, a methoxy group.

This example also demonstrated that the reaction can be successful when the mole ratio of Grignard/di-halogenated aromatic is less than 2/1, as in this case where the ratio was 1.77/1.

The coupling reaction flask and set up were the same as described in example 3. The flask was charged with anhydrous NiBr2 0.55 grams/2.5 mmole, TPP 6.55 grams/25 mmole, 2,6-dichloroanisole 17.7 grams/0.10 mole, reagent grade o-xylene 50 ml 44.3 grams. A green solution of the NiBr2/TPP complex was formed by heating the mixture to reflux and holding it at reflux for 30 minutes. After cooling to 50 degrees C., 150 ml of dry THF solvent was added. A 250 ml pressure equalizing addition funnel was charged with 177 ml of 1.0 molar 2-chloromagnesiumtoluene/0.177 mole and placed in the center neck of the reaction flask.

The coupling reaction was carried out at 50 degrees Celsius by the dropwize addition of the Grignard reactant to the flask over 2 hours. The mixture was stirred an additional hour following the addition of the Grignard. The solution was a dark red-brown color at the end of the addition. After cooling to ambient temperature, the reaction was treated with 35 ml of concentrated hydrochloric acid and 115 ml of deionized water, followed by the addition of 3 ml of 50% aqueous hydrogen peroxide. Two liquid layers resulted, an orange upper organic layer and very pale green aqueous layer. These were separated in a separatory funnel with the discarding of the aqueous layer. The organic layer was washed with two portions of 100 ml of 1% aqueous NaCl. A sample of the organic layer was collected for gas chromatographic analysis and GC-MS identification of the mixture components.

Based on the gas chromatographic analyses of the crude product, the following yields are given based on the amount of Grignard added.
Conversion of 2,6-dichloroanisole=96%
Selectivities of Grignard reactant to a given product:
Toluene=9.0%
2,2'-Dimethyl-1,1'-biphenyl=18.3%
2-Methyl-2'-methoxy-3'-chloro-1,1'-biphenyl=0.5% (mono-arylated product)
2,2"-Dimethyl-2'-methoxy-1,1':3',1"-terphenyl=72.2% (diarylated product)

The crude organic layer was stripped with nitrogen to remove the THF and then dissolved in 100 ml of toluene. This solution was passed through a 2.5 cm×7.5 cm diameter bed of Brockmann I alumina and washed through with an additional 300 ml of toluene. The toluene and most of the lower boiling impurities were removed overhead by vacuum distillation in a 2 cm diameter by 20 cm vacuum jacketed Vigreux column operating at 0.5 kPa with a maximum base temperature of 170 degrees Celsius. Upon cooling, the base product weighing 19.9 grams crystallized. This material was recrystallized from a refluxing mixture of 60 ml of absolute methanol and 10 ml of n-propanol and cooling to ambient temperature. The resulting white crystals were washed with three 10 ml portions of fresh solvent of the same composition. After drying under vacuum, a net weight of 9.93 grams or 39% of theoretical yield of desired pure product was obtained.

The proton NMR analysis of the pure product expressed as ppm relative to TMS:

11H (overlapping multiplets) 7.15-7.30 ppm aromatic C—H; 3H (S) 3.04 ppm —OCH3; 6H (S) 2.20 ppm 2,2" benzylic CH3.

Example 7—Preparation of 1,3,5-Tri(2'-methylphenyl-1'-yl)benzene by Reaction of 2-Chloromagnesiumtoluene with 1,3,5-Trichlorobenzene in the Presence of 10/1 Mole Ratio TPP/NiBr2

This is an example of the coupling addition of three aryl groups to a trichloro aromatic hydrocarbon by the catalyst of this disclosure.

The 1 liter coupling reaction flask was equipped as described in example 3. The flask was charged with anhydrous NiBr2 0.55 grams/2.5 mmole, TPP 6.55 grams/25 mmole; 1,3,5-trichlorobenzene 18.31 grams/0.10 mole and 50 ml/44.3 grams of reagent grade o-xylene. The green solution of the NiBr2/TPP catalyst was formed by heating the mixture to reflux and holding at reflux for 30 minutes. After cooling to ambient temperature, 100 ml of dry THF solvent was added. The 500 ml pressure equalizing addition funnel was charged with 320 ml of 1.0 molar 2-chloromagnesiumtoluene solution in THF (Aldrich) 0.32 mole. This represents a 3.2/1 mole ratio of Grignard/trichloroaryl or about a 7 mole % excess of Grignard. A sample of the starting mixture was taken for gas chromatographic analysis (sample #1).

The coupling reaction was carried out at 50 degrees Celsius by the dropwize addition of the Grignard reactant over 2 hours and 50 minutes. The addition of the Grignard solution turned the mixture to a red-brown color. The mixture was stirred an additional 2 hours at 50 degrees Celsius following the complete addition of the Grignard. Additional samples were taken at 41% of the Grignard addition (sample #2); immediately following the complete addition of Grignard (sample #3); after 2 hours of additional stirring (sample #4) and following the acid hydrogen peroxide quench (sample #5). The table below lists the amount in grams of a given material in the reaction flask on the basis of gas chromatographic analysis. Sample #5 was also submitted for GC-MS analysis for identification of the individual components. This analysis was unable to find any traces of the mono-arylation intermediate product, a testament to the efficiency of the catalyst of this disclosure to poly-arylate multi-halogenated aromatic compounds.

| Compound Weights in Grams in Reaction Mixture | | | | | |
| --- | --- | --- | --- | --- | --- |
| Sample | Toluene | 1,3,5-TCBz | 2,2'-Bitolyl | DiArylated | TriArylated |
| 1 | 0.00 | 18.31 | 0.00 | 0.00 | 0.00 |
| 2 | 1.37 | 9.71 | 1.34 | 2.07 | 11.74 |
| 3 | 5.31 | 0.64 | 3.86 | 1.71 | 30.07 |
| 4 | 3.06 | 0.00 | 4.73 | 0.30 | 33.59 |
| 5 | 2.78 | 0.00 | 5.28 | 0.12 | 34.55 |

The crude product solution was treated with 35 ml of concentrated hydrochloric acid and 115 ml of deionized water, followed by the addition of 3 ml of 50% aqueous hydrogen peroxide. The two liquid phases were separated in a funnel and the yellow organic layer was washed with two 100 ml portions of 1% aqueous NaCl solution. The organic layer was subjected to nitrogen stripping followed by vacuum at 0.5 kPa pressure while warming the flask to about 50 degrees Celsius to remove all the THF and most of the o-xylene. The sticky solid was dissolved in a mixture of 200 ml of isomeric hexane and 50 ml of toluene. This was passed through a 2.5 cm by 7.5 cm diameter bed of Brockmann I alumina and the bed washed through with a total of 300 ml of a 2/1 v/v mixture of isomeric hexane/toluene. The clear colorless filtrate was stripped with nitrogen to a white sticky waxy solid. This material was recrystallized from 100 ml of refluxing isomeric hexane and cooling to ambient temperature. The white crystals were washed with two 25 ml portions of cold isomeric hexane and dried under 0.5 kPa vacuum. The net weight of pure product was 21.14 grams representing 60% theoretical yield based on 1,3,5-trichlorobenzene.

The proton NMR spectrum ppm relative to TMS: 3H (S) 7.31 ppm 2,4,6 aromatic C—H; 12H (overlapping doublets) 7.30-7.32 ppm aromatic C—H on outside aromatic rings; 9H (S) 2.415 ppm benzylic CH3.

Example 8—Preparation of 2,2',2'',5'-Tetramethyl-1,1':4',1''-terphenyl by Reaction of 2-Chloromagnesiumtoluene with 2,5-Dibromo-p-xylene in the Presence of 10/1 TPP/NiBr2

This preparation represents a diarylation reaction that prepares a hydrocarbon having four methyl groups present using the catalyst of this disclosure.

The coupling flask and configuration is the same as described in example 3. The flask was charged with anhydrous NiBr2 0.55 grams/2.5 mmole, TPP 6.55 grams/25 mmole, 2,5-dibromo-p-xylene 52.8 grams/0.20 mole and 50 ml/44.3 grams of reagent grade o-xylene. The green solution of the NiBr2/TPP complex was formed as normal by heating the mixture to reflux for thirty minutes. After cooling to 50 degrees Celsius, 150 ml of dry THF solvent was added. The 500 ml pressure equalizing addition funnel was charged with 400 ml of 1.0 molar 2-chloromagnesiumtoluene solution in THF/0.40 mole and placed on the center neck of the flask.

The coupling reaction was carried out at 50 degrees Celsius by the dropwize addition of the Grignard reactant to the flask over 2 hours and 45 minutes. The reaction mixture turned to red-orange and then brown during the course of the addition. Following the complete addition, the flask was stirred at 50 degrees Celsius for an extra hour and then cooled to ambient temperature. Gas chromatographic samples were taken at 0%; 50%; immediately after completion of the Grignard addition; one hour following completion and after the hydrochloric acid and hydrogen peroxide treatment. The retention times of the 2,5-dibromo-p-xylene and 2,2'-bitolyl were equivalent, which precluded the measure of these materials. Also, the elution time of the tetramethyl material was equivalent to that of TPP which also precluded the measurement of this material until after oxidation of the TPP was carried out. The final sample was also submitted for GC-MS analysis. On the basis of Grignard added the following weights in grams in the crude mixture and selectivities of product from Grignard reactant are listed below:

Toluene=5.68 grams=15.4% selectivity
2,2',5'-Trimethyl-4'-bromo-1,1'-biphenyl (monarylation product)=8.34 grams=7.6% selectivity
2,2',2'',5'-Tetramethyl-1,1':4',1''-terphenyl (diarylation product)=33.78 grams=59% selectivity The conversion of 2,5-dibromo-p-xylene and amount of 2,2'-bitolyl formed could not be measured.

The crude reaction product was treated with 35 ml of concentrated hydrochloric acid and 115 ml of deionized water followed by the addition of 3 ml of 50% aqueous hydrogen peroxide. After separation in a funnel, the organic layer was washed with two 100 ml portions of 1% aqueous NaCl solution. Toluene, 100 ml, had to be added during the washing step to prevent product crystallization from the solvent mixture.

The crude organic material was then stripped with nitrogen and then subjected to 0.5 kPa vacuum at 60 degrees C. to remove the bulk of the lower boiling impurities. The net weight of sticky pale yellow crystals was 73 grams. This material was dissolved in 200 ml of isomeric hexane at reflux and cooled with stirring to ambient temperature. The desired product crystallized. This was then filtered on a coarse glass frit and the crystals were washed with four 50 ml portions of isomeric hexane. After drying in vacuum, a net weight of 18.11 grams of desired white crystalline product, representing 31% of theoretical yield, was obtained. The material was 97% pure by gas chromatographic analysis.

The proton NMR spectrum in ppm relative to TMS: 2H (S) 6.98 ppm 2',5' aromatic C—H; 8H (overlapping doublets) 7.15-7.30 ppm aromatic C—H of outer rings; 6H (S) 2.12 ppm 2,2'' benzylic CH3; 6H (S) 2.02 2',5' benzylic CH3.

I claim:
1. A method of preparing aromatic hydrocarbons for use as precursors for catalyst ligands, the method comprising:
providing a nickel based catalyst solution;
providing a polyhalogenated aromatic hydrocarbon comprising at least two reactive halogen groups on its ring;
combining the nickel based catalyst solution and polyhalogentated aromatic hydrocarbon to form a mixture; and
adding a Grignard reactant to the mixture to form an aromatic hydrocarbon as a precursor for the preparation of catalyst ligands, wherein the nickel based catalyst solution is prepared by the reaction of a nickel source with a triarylphosphine and the yield of aromatic hydrocarbon is 84% or higher
wherein the method is illustrated by the following general reaction:

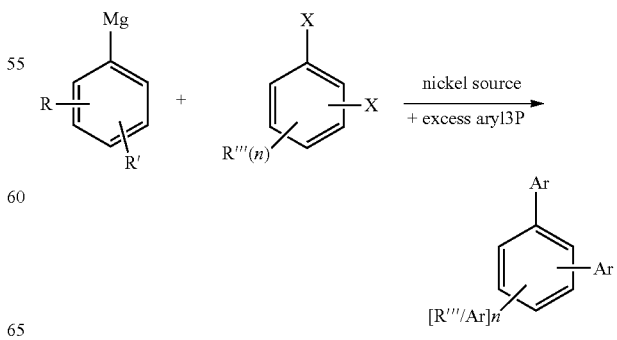

wherein,
R=CH3; aryl; alkylaryl; alkyl; alkyl or aryl ether; H; thioether, or perfluoroalkyl
R'=CH3; aryl; alkylaryl; alkyl; alkyl or aryl ether; H; thioether, or perfluoroalkyl
X=reactive halogen groups
R'''=R, R' and/or X
n=0 to 4
P=Phosphorous atom
Aryl3P=Triarylphosphine
Ar=Grignard aromatic moiety
/=and/or
Halo2=chloride or bromide
nickel source=(TPP)2Ni(II)X2; or anhydrous Ni (II) chloride or bromide
TPP=triphenylphosphine.

2. The method of claim 1 wherein the triarylphosphine is triphenylphosphine.

3. The method of claim 1, wherein a mole ratio of triarylphosphine/Ni is comprised of a range from about 2.2/1 up to about 100/1.

4. The method of claim 1, wherein the mole ratio of triarylphosphine/Ni is comprised of a range from about 10/1 up to about 100/1.

5. The method of claim 1, wherein the mole ratio of triarylphosphine/Ni is about 5/1 up to about 10/1.

6. The method of claim 1, wherein the triarylphosphine is tri(orthotolyl)phosphine, tri(p-methylphenyl)phosphine, diphenyl(o-tolyl)phosphine, diphenyl(p-methylphenyl)phosphine, or di-o-tolylyl(phenyl)phosphine.

7. The method of claim 1, further comprising adding coupling co-solvent to the mixture of the nickel based catalyst solution and polyhalogentated aromatic hydrocarbon to facilitate coupling of the mixture with the Grignard reactant.

8. The method of claim 7, wherein the coupling co-solvent is diethyl ether.

9. The method of claim 7, wherein the coupling co-solvent is tetrahydrofurane.

10. The method of claim 1, wherein the Grignard reactant is prepared by reacting a bromo or chloro aromatic hydrocarbon with magnesium metal in a solvent.

11. The method of claim 10, wherein the solvent comprises diethyl ether, tetrahydrofurane, di-n-propyl ether, di-n-butyl ether or 1,4-dioxane.

12. The method of claim 1, wherein the mole ratio of Ni/Grignard aromatic moiety is comprised of a range from about 1/10 up to about 1/1000.

13. The method of claim 12, wherein the mole ratio of Ni/Grignard aromatic moiety is comprised of a range from about 1/100 up to about 1/200.

14. The method of claim 1, wherein the Grignard reactant is added to the mixture in an anaerobic environment free of moisture.

15. The method of claim 1, wherein the Grignard reactant is added to the mixture in a temperature range of from about 0 degrees Celsius to about 100 degrees Celsius.

16. The method of claim 15, wherein the Grignard reactant is added to the mixture in a temperature range of from about 25 degrees Celsius to about 65 degrees Celsius.

17. The method of claim 1, illustrated by the following specific reaction:

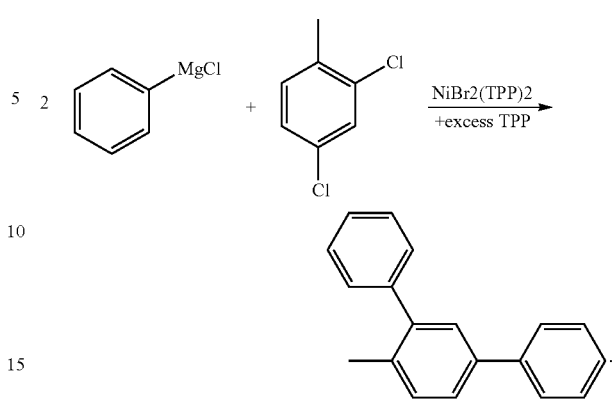

18. The method of claim 1, illustrated by the following specific reaction:

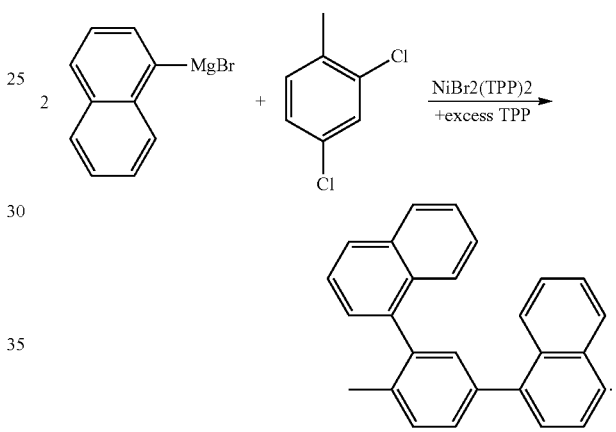

19. The method of claim 1, illustrated by the following specific reaction:

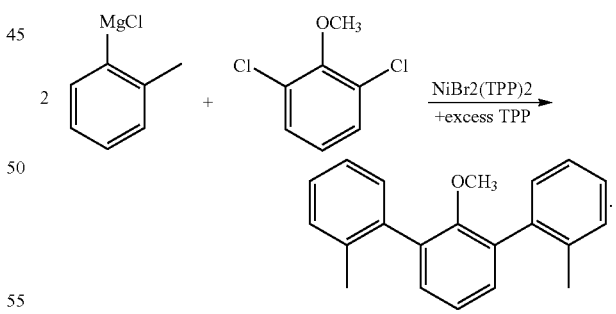

20. The method of claim 1, illustrated by the following specific reaction:

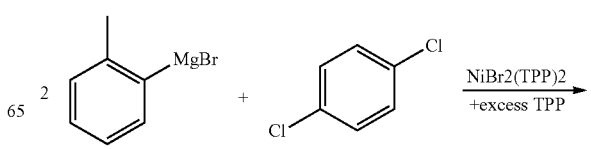

-continued
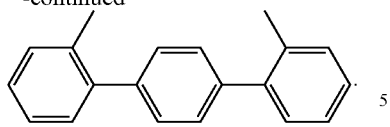
21. The method of claim 1, illustrated by the following specific reaction:
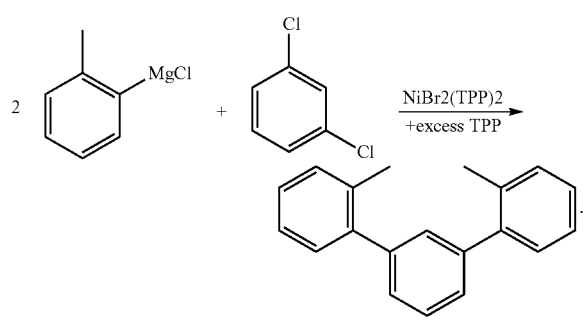
22. The method of claim 1, illustrated by the following specific reaction:
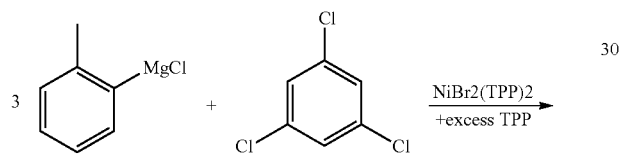
-continued
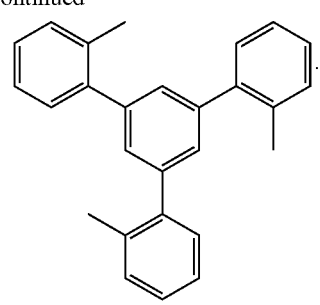
23. The method of claim 1, illustrated by the following specific reaction:
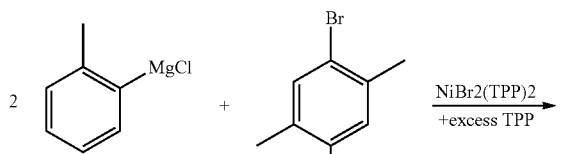
* * * * *